United States Patent [19]

Franke

[11] 4,384,359
[45] May 17, 1983

[54] TOMOGRAPHIC APPARATUS FOR THE PRODUCTION OF TRANSVERSE LAYER IMAGES

[75] Inventor: Kurt Franke, Erlangen, Fed. Rep. of Germany

[73] Assignee: Siemens Aktiengesellschaft, Berlin & Munich, Fed. Rep. of Germany

[21] Appl. No.: 206,136

[22] Filed: Nov. 12, 1980

[30] Foreign Application Priority Data

Dec. 19, 1979 [DE] Fed. Rep. of Germany ....... 2951222

[51] Int. Cl.³ .............................................. G03B 41/16
[52] U.S. Cl. ......................................... 378/9; 378/105
[58] Field of Search ........................ 250/445 T; 378/9

[56] References Cited

U.S. PATENT DOCUMENTS

| | | | |
|---|---|---|---|
| 3,952,201 | 4/1976 | Hounsfield | 250/445 T |
| 4,192,997 | 3/1980 | Baumann | 250/445 T |
| 4,200,797 | 4/1980 | Bax | 250/445 T |

Primary Examiner—Craig E. Church
Attorney, Agent, or Firm—Hill, Van Santen, Steadman, Chiara & Simpson

[57] ABSTRACT

In an exemplary embodiment, a medium frequency generator is mounted on the rotating frame together with at least one x-ray tube, preferably, however, a plurality of x-ray tubes. The x-ray tubes are grid-controlled and, together with their filament transformer are provided in one separate housing each. A grid control circuit is connected with the component parts on the rotating frame.

1 Claim, 1 Drawing Figure

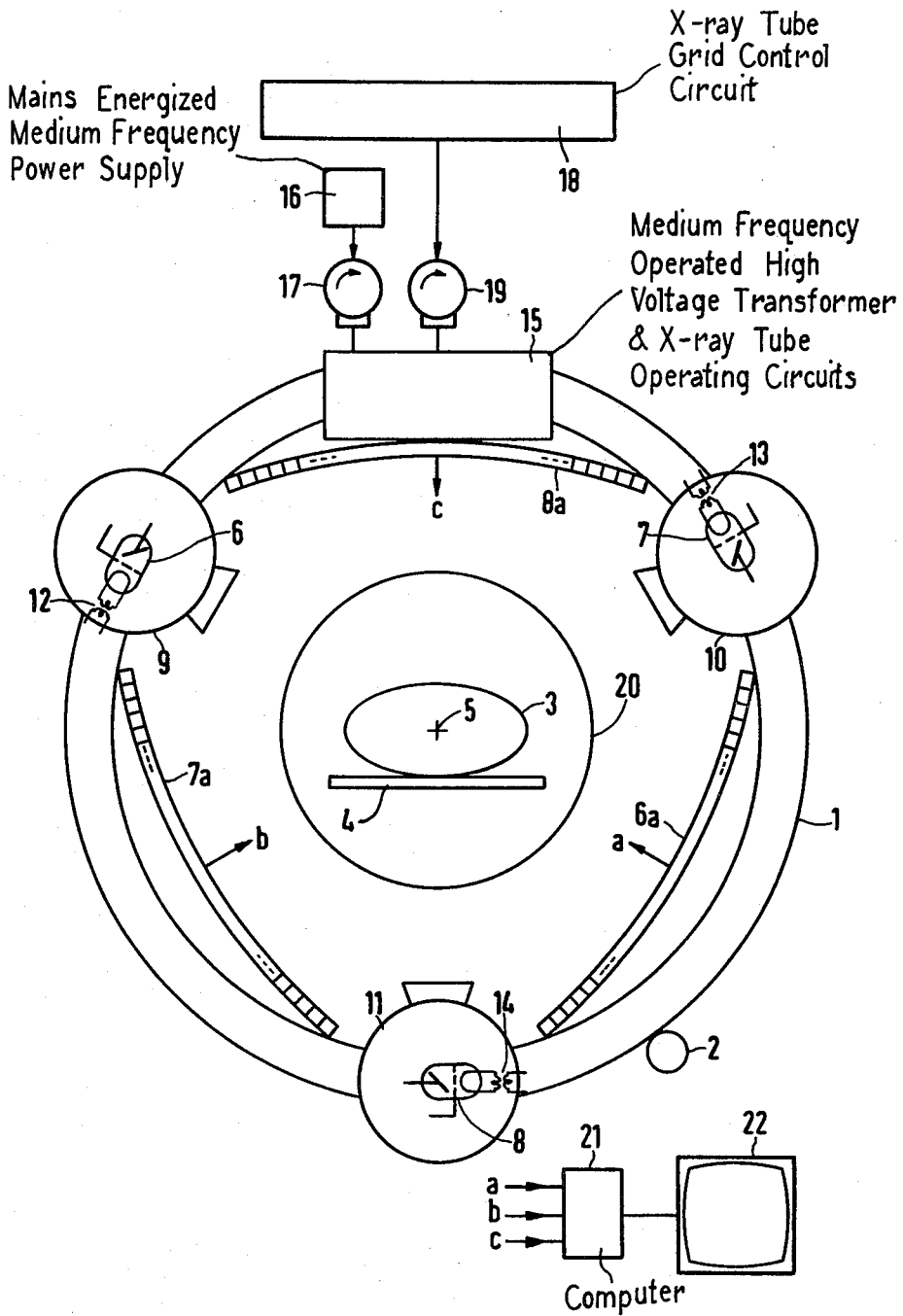

TOMOGRAPHIC APPARATUS FOR THE PRODUCTION OF TRANSVERSE LAYER IMAGES

BACKGROUND OF THE INVENTION

The invention relates to a tomographic apparatus for the production of transverse layer images of a radiography subject comprising an x-ray measuring arrangement with at least one x-ray source which is fed by an x-ray generator, which x-ray source generates an x-ray beam penetrating the radiography subject, the cross-sectional extent of said x-ray beam, perpendicular to the layer plane, being approximately equal to the layer thickness, and with a radiation receiver which determines the radiation intensity behind the subject, a rotating frame for rotating the x-ray source in the layer plane for the scanning of the radiography subject from different projections, and a measured value converter for the transformation of the signals delivered by the radiation receiver into a layer image, in which tomographic apparatus the high voltage transformer for the x-ray tube is operated with a medium frequency which is higher than the mains frequency and at least the component parts of the x-ray high voltage generator which are on the high voltage side are mounted on the rotating frame.

A tomographic apparatus of this type is described in the German OS No. 27 50 633 (U.S. Pat. No. 4,192,997 issued Mar. 11, 1980). In the case of this tomographic apparatus, a rapid movement of the x-ray source for scanning of a radiography subject is possible, because the high voltage-side components of the x-ray generator are mounted with the medium frequency generator on the rotating frame and are rotated together with the x-ray source during scanning of the radiography subject. Thus, no high voltage cables need be run to the x-ray source. The design of the x-ray high voltage supply to utilize a medium frequency generator results in the high voltage transformer being capable of being designed to be small and light-weight, so that for scanning of a radiography subject no large masses need be accelerated and braked. During the scanning of the radiography subject from different projections it is expedient to briefly switch on the x-ray tube for one projection in each instance, so that, in the case of 360 projections, for example, it is briefly switched on 360 times per scan cycle.

SUMMARY OF THE INVENTION

The object underlying the invention resides in designing a tomographic apparatus of the type initially cited such that a very rapid switching-on and -off of the x-ray tube can take place, so that the rotational speed of the rotating frame can be high.

In accordance with the invention, this object is achieved in that, as the radiation source, a grid-controlled x-ray tube together with its filament transformer is provided in a separate housing, and that a grid control circuit is connected with the components on the rotating frame. In the inventive tomographic apparatus, the switching of the x-ray tube proceeds via a control grid which permits very short switching times and a high rotational speed of the rotating frame. It is expedient here, with the supply of control pulses to the control grid, to also supply control pulses to the high voltage generator on the rotating frame which disconnect the high voltage at the x-ray tube in the case in which the x-ray tube conducts no current (during cut-off condition at the control grid). The control grid on the x-ray tube has the advantage that it also permits a very precise control of the x-ray tube current. Via the x-ray tube current a control of the x-ray tube voltage is also possible due to the voltage drop in the circuit for supplying the x-ray tube.

The invention shall be explained in greater detail in the following on the basis of an exemplary embodiment illustrated in the drawing; and other objects, features and advantages will be apparent from this detailed disclosure and from the appended claims.

BRIEF DESCRIPTION OF THE DRAWING

The single FIGURE is a diagrammatic view of tomographic apparatus in accordance with the present invention.

DETAILED DESCRIPTION

In the drawing a rotating frame 1 is illustrated which is rotatable about a center 5 by means of a drive device 2 for scanning a transverse layer of a patient 3 lying on a support 4. On the rotating frame 1, in the example, three x-ray tubes 6, 7, 8 are arranged, each of which being disposed in a respective housing 9, 10, 11. In the housing for the grid-controlled x-ray tubes 6, 7, 8 also the filament transformers 12, 13, 14 are arranged.

In order to supply the x-ray tubes 6, 7, 8 with filament-and high-voltage, a medium frequency operated high voltage generator 15 is mounted on the rotating frame 1, which receives its input voltage from a mains apparatus 16 via a rotating current coupling 17. In addition, a grid control circuit 18 is present which, via a rotating current coupling 19, activates the high voltage generator 15 and the x-ray tubes 6, 7, 8 via their control grids.

Each of the x-ray tubes 6, 7, 8 emtis a fan-shaped x-ray beam which, with its marginal rays, is tangent to a radiography subject circle 20 and strikes an opposite radiation receiver 6a, 7a, 8a. Each radiation receiver 6a, 7a, 8a is comprised of a series of individual detectors, for example 512 individual detectors, respectively, each of which converts the received radiation intensity into a corresponding electric signal. Each x-ray beam is so dimensioned in its cross-sectional extent that its thickness perpendicular to the layer plane is equal to the layer thickness.

The output signals of the radiation receivers 6a, 7a, 8a, which are produced with every projection, are supplied to a computer or measured value converter 21 which determines therefrom the attenuation values of predetermined points of the examined transverse layer and effects their image-reproduction on a display unit 22.

The examination of the patient 3 proceeds in such a fashion that the rotating frame 1, with the component parts arranged thereupon, is rotated through an angle of 120° and, with each degree, the x-ray tubes 6, 7, 8 are successively switched on. In this manner, in each angular increment of movement of the rotating frame 1, a total of 3×512 detector output signals, and, as a result of a complete scanning, 3×512×120 detector output signals are supplied to the computer 21. The switching of the x-ray tubes 6, 7, 8 proceeds from the grid control device 18 via the control grids. A rapid switching is thereby possible even in the case of a rapid rotation of the rotating frame 1. During the time when an x-ray tube conducts no current, expediently also the high voltage generator 15 is so influenced from the grid control circuit 18 that the high voltage is removed from the x-ray tube.

The x-ray tubes 6, 7, 8 and their filament transformers 12, 13, 14 are permanently wired on the rotating frame 1 with the high voltage generator 15, whose supply frequency lies in the kHz-range between approximately one and fifteen kilohertz (1 and 15 kHz).

Via the control grids, it is also possible to control the x-ray tube current when the x-ray tube is switched on or to keep the x-ray tube voltage constant via the x-ray tube current.

The number of x-ray tubes is not essential for the present invention. It is also possible to arrange only one, or two, x-ray tubes on the rotating frame 1.

In the example, rotating current couplings 17 and 19 for the supply and control of the high voltage generator 15 and the x-ray tubes 6, 7, 8 are provided. It is also possible to connect the high voltage generator 15 via cables with the associated power supply and control installations, which cables can be comparatively light-weight because they are not high voltage cables. Also the connection of the radiation receivers 6a, 7a, 8a to the computer 21 can proceed via low voltage cables. However, it is also conceivable to provide a known, stationary detector ring as the radiation receiver which surrounds the x-ray tubes 6, 7, 8 on the exterior, or which is arranged in the rotating frame 1 and is swiveled such that, in each instance, only one part, detecting the radiation to be received, is pivoted into the radiation, such as is described in the German OS No. 27 14 759.

It will be apparent that many modifications and variations may be effected without departing from the scope of the novel concepts and teachings of the present invention.

SUPPLEMENTARY DISCUSSION

The component 15 on the rotating frame 1 may include a direct current LC filter, an inverter or medium frequency generator, and a high voltage transformer as shown in the fifth figure of U.S. Pat. No. 4,192,997. In this case, the high voltage circuit on the rotating frame 1 includes the secondary of the transformer, a high voltage rectifier and at least one grid controlled x-ray tube. The mains frequency rectifier may also be carried on the rotating frame, in which case coupling 17 transfers mains frequency energy, as shown in the sixth figure of U.S. Pat. No. 4,192,997. Alternatively only the high voltage circuit components may be carried in the rotating frame 1, as shown in the fourth figure of U.S. Ser. No. 094,766 filed Nov. 16, 1979, so that coupling 17 transfers medium frequency energy.

The x-ray tube high voltage may be interrupted in response to each grid turn-off interval via the closed loop high voltage control circuit controlling the inverter on the rotating frame 1, such a control circuit with a voltage control input (at nineteen) being shown in the fifth and sixth figures of U.S. Pat. No. 4,192,997. An individual inverter and high frequency transformer-rectifier may be associated with each grid-controlled x-ray tube so that each tube then has an individual x-ray high voltage shut off circuit operating in synchronism with cut-off of the respective grid circuit. The grids may be switched on sequentially during each one degree of travel of the rotating frame during a scanning operation.

I claim as my invention:

1. Tomographic apparatus for the production of transverse layer images of a radiography subject, comprising a radiation measuring arrangement with a plurality of x-ray sources each of which generates an x-ray beam penetrating the radiography subject, the cross-sectional extent of each said x-ray beam, perpendicular to the layer plane, being approximately equal to the layer thickness, and with a radiation receiver which determines the radiation intensity behind the subject, a rotating frame for rotating the x-ray sources in the layer plane for the scanning of the radiography subject from different projections, and a measured value converter for transformation of the signals delivered by the radiation receiver into a layer image, a high voltage transformer operated with a medium frequency which is higher than the mains frequency, a high voltage circuit for energizing said plurality of x-ray sources, said high voltage circuit (15) being mounted on said rotating frame and comprising the secondary of the x-ray high voltage transformer, said plurality of x-ray sources comprising grid-controlled x-ray tubes (6, 7, 8) each connected with said high voltage circuit, filament transformers (12, 13, 14) for respectively supplying filament current to said grid-controlled x-ray tubes, a plurality of separate housings (9, 10, 11) on said rotating frame containing said grid-controlled x-ray tubes and said filament transformers, and a grid control circuit (18) connected with the grids of said grid-controlled x-ray tubes on the rotating frame (1) for controlling pulsing operation of said x-ray sources during scanning.

* * * * *